United States Patent [19]

Thompson et al.

[11] Patent Number: 5,641,844
[45] Date of Patent: Jun. 24, 1997

[54] POLYMERS WITH CRYSTALLIZABLE FLUOROPOLYMERS

[75] Inventors: Robert M. Thompson; Ya Xi Shen, both of Wilmington, Del.

[73] Assignee: W. L. Gore & Associates, Inc., Newark, Del.

[21] Appl. No.: 571,376

[22] Filed: Dec. 13, 1995

Related U.S. Application Data

[60] Provisional application No. 60/002,097, Aug. 10, 1995.

[51] Int. Cl.$^6$ ............................. C08F 18/20; B05D 5/00
[52] U.S. Cl. ...................... 526/245; 427/244; 427/389.9; 427/392; 427/393.5
[58] Field of Search ........................... 526/245; 427/244, 427/389.9, 392, 393.5

[56] References Cited

U.S. PATENT DOCUMENTS

| | | |
|---|---|---|
| 3,171,861 | 3/1965 | Ahlbrecht . |
| 3,282,905 | 11/1966 | Fasick et al. . |
| 3,462,296 | 8/1969 | Raynolds et al. . |
| 3,997,507 | 12/1976 | Kirimoto et al. . |
| 4,147,551 | 4/1979 | Finnicum et al. . |
| 4,147,851 | 4/1979 | Raynolds . |
| 4,559,754 | 12/1985 | Bacon . |
| 4,716,208 | 12/1987 | Korzeniowski . |
| 4,742,140 | 5/1988 | Greenwood et al. . |
| 4,859,754 | 8/1989 | Maekawa et al. . |
| 5,149,753 | 9/1992 | Inukai et al. ................... 526/245 |

FOREIGN PATENT DOCUMENTS

| | | | |
|---|---|---|---|
| 0408917 | 1/1991 | European Pat. Off. ............... 526/245 |
| 2058513 | 2/1990 | Japan ..................................... 526/247 |

OTHER PUBLICATIONS

Zonyl Fluorochemical Intermediates (DuPont Co.) pp. 1–24.
Journal of Paint Technology, vol. 44, pp. 42–57, (1972) – William A. Zisman.
Journal of Applied Science, vol. 13, pp. 1741–1747 (1969) – D. K. Owens.
Chemtech, Mar. 1982 – Practicing Polymer Surface Chemistry – A Stream of Consciousness – David Dwight.
Efficient Polymerization of a Semi–Fluorinated Liquid Crystalline Methacrylate – Hoyle, et al., Polymer 1993, vol. 34, No. 14, pp. 3070–3074.
Synthesis and Mesoscopic Organization of Perfluoroalkyl–Alkylene Methacrylate Monomers – Hopken, et al., Mol. Cryst. Liq. Cryst., 1992, vol. 210, pp. 59–73.

*Primary Examiner*—Joseph L. Schofer
*Assistant Examiner*—N. Sarofim
*Attorney, Agent, or Firm*—Gary A. Samuels

[57] ABSTRACT

This invention relates to polymers having pendant side groups of:

$$-(CH_2)_m-(CF_2)_nF$$

wherein m is 10, and n is 10 and more in which the amount of the monomer containing the moiety $-(CF_2)_{10}F$ constitutes about 50% or more of the total percent of all the monomers. By adjusting the number of $-CH_2-$ groups to 10 and adjusting the distribution within the $-(-CF_2)_mF$ groups, it has been discovered that the particular side group configuration forms crystalline regions that reduce mobility of the side chains and thereby improves the repellency of materials coated with the polymers of the invention.

10 Claims, No Drawings

POLYMERS WITH CRYSTALLIZABLE FLUOROPOLYMERS

CROSS REFERENCE TO RELATED APPLICATION

This application claims the benefit of Provisional Application No. 60/002,097, filed Aug. 10, 1995.

FIELD OF THE INVENTION

This invention relates to polymers which contain crystallizable fluorocarbon side chains, and to their monomers, which polymers provide durable water and oil repellency to substrates coated with the polymers.

BACKGROUND OF THE INVENTION

Fabrics treated with water repellents tend to lose repellency upon exposure to liquid water, such as rain showers or laundering; and upon exposure to soiling substances, such as oils. Several patents address these problems but without significant success, such as U.S. Pat. No. 4,859,754, 4,716,208, 4,147,851 and 3,997,507. These patents describe copolymers of acrylates or methacrylates having perfluoroalkyl groups, and either amphipathic monomers (U.S. Pat. No. 4,559,754), chlorohydroxypropyl acrylates or methacrylates (U.S. Pat. No. 4,716,202), dialkylamines alkyl acrylates or methacrylates (U.S. Pat. No. 4,147,551) or alkylvinyl ethers (U.S. Pat. No. 3,997,507).

Polymers of acrylic or methacrylic acid esters that have pendant fluoroalkyl side groups are useful as water/oil repellents. The fluoroalkyl groups have the formula $-(CH_2)_m-(CF_2)_nF$ and typically the polymer will have a distribution of chain lengths wherein n ranges from 4, 6, 8, 10, 12 etc. The component of largest concentration in the polymer is usually predominantly either n=6 or 8 (e.g., typically distributions are by weight, $C_4$, 4%; $C_6$ 33%; $C_8$, 30%; $C_{10}$, 15%; $C_{12}$ 8%; etc. or $C_6$, 2%; $C_8$, 51%; $C_{10}$, 31%; $C_{12}$, 11%; etc.). See for example, DuPont Product Literature "Zonyl" Fluorochemical Intermediates.

These polymers can be homopolymers or can be copolymers of the fluoromonomers with other monomers which do not generally detract from the repellent performance, but add other characteristics such as improved film formation or emulsion stability. The distribution of the fluoroalkyl side chain lengths depends on the manufacturing techniques, and the telomers of tetrafluoroethylene used.

The water and oil repellency imparted to substrates coated with these polymers is due to the perfluoroalkyl component, $F(CF_2)-_n$ of the side chain with its terminal $CF_3$ group. Contact angle measurements carried out by Zisman (Journal of Paint Technology Vol. 44, pp. 42–57 (1972)) indicated these groups have the lowest critical surface tension of wetting known, about 6 dynes/cm., based on perfluorolauric acid monolayer. In addition, A. Owens and R. Wendt have shown (J. App. Poly. Sci. 13 1141 (1969)) that long chain perfluoroalkyl groups have surface energies of 7.8–8 dynes/cm, again a very low surface energy measurement. In the case of fluoroacrylate polymers, the low surface energy of substrates coated with the polymer results from the perfluoroalkyl side chains of the polymers being oriented normal i.e. perpendicular to the surface of the substrate. This maximizes the $-CF_3$ concentration at the solid/air interface.

However, these polymers tend to lose their effectiveness as repellents over time in contact with water. The loss of repellency can be explained by the molecular rearrangement of these side chains to find a new level of surface energy in a water environment. This alteration of position of the side chains results in a reduction in concentration of the $-CF_3$ terminal groups at the surface because the $-CF_3$ groups move away from the most advantageous repellency configuration. Thus, it has long been a defect in existing fluoroalkylacrylate polymers that the oil and water resistance is not as good as it could be because of the mobility of the fluoroalkyl side chains, resulting in the side chains moving or rotating to a less desirable configuration, i.e., to a less chemically uniform configuration on the surface of a substrate. The most desirable configuration is one in which the side chains, as stated above, stick out away from the substrate surface so that the end $-CF_3$ groups present a chemically uniform barrier to water or oil molecules.

SUMMARY OF THE INVENTION

It is desirable to prevent mobility of aligned fluoroalkyl side chains and to hold or lock them in a "crystalline" type configuration, in order to prevent loss of oil and water repellency upon exposure to liquid water. This invention provides such polymers and the monomers from which the polymers are prepared in which the fluoroalkyl side chains are stabilized and are restricted from movement upon exposure to water.

Thus this invention is directed to organic monomers and to polymers of the monomers having a crystallizable fluorocarbon terminal segment, which segment has the formula $-(CH_2)_m-(CF_2)_nF$ wherein m is 10 and n is a mixture of integers of 10 and more in which the amount of the monomer containing the moiety $-(CF_2)-_{10}F$ constitutes at least about 50% or more of the total weight of all the monomers present.

It is known that it is difficult and costly to prepare a pure monomer with a terminal group $-(CF_2)_nF$ where n is a single numeral. In preparing these monomers, the result is more commonly a mixture of monomers where the $-(CF_2)_nF$ group varies in n. Predominately in any one m mixture of commercially available monomers n is usually 6, 8, 10, 12, etc.

Representative monomers include fluoroalkylacrylate and methacrylates represented by the formula

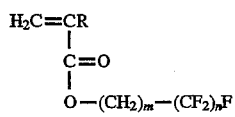

where R is $-H$ or $-CH_3$, m is 10 and n is defined as above.

The invention is also directed to polymers of the monomers useful as coatings on substrates.

Representative polymers include polymers containing acrylate or methacrylate recurring units. These are represented by the formula

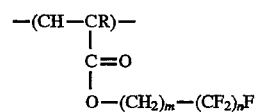

where R, m and n are as defined above.

It has been discovered that adjusting the number of $-CH_2-$ groups in the side chain and adjusting the distribution of n within the $-(CF_2)_nF$ groups in the side chain can result in alignment of the side chains in the polymers, and thus in formation of crystalline-like regions. This formation results in limited movement of the side chains and thereby provides improved durability of oil and water repellency to materials coated with the polymers. When m is 10, the —$CH_2$— groups are of an optimum length believed to facilitate alignment in generally parallel rows of the fluoroalkyl side chains. In addition, it has been found that when shorter —$(CF_2)_n$—F chains such as when n is 4, 6 or 8 are eliminated from the distribution of the side chains, the remaining —$(CF_2)_n$F groups result in better alignment and crystallization. These crystalline regions are relatively immobile under normal end use conditions and thus the perfluoroalkyl side chain moieties of the polymer remain perpendicular to the surface of the substrate. It has also been found that the $(CF_2)_n$— chain cannot be too long, or else the polymer will have too high a melting point for ease of coating and working. Thus, m should be 10 and n should be 10 or more with n equal 10 being at least about 50% of the n distribution, and the melting point of the polymer should be between 80° C. and 150° C., preferably between 90° C. and 110° C.

An indication of durability of the water and oil repellent coatings of the invention can be obtained by determining the receding contact angle. (See M. Morro, et al. "Advances in Colloid and Interfacial Sciences 32, 79–116 (1990)). It is known that the higher the receding contact angle the more chemically uniform the fluoroalkyl side chains. The contact angle data can be transformed into (1+cos θ) values, and it is preferable to do so because (1+cos θ) is directly proportional to the energy levels of the polymer. It has been determined that good durability of repellency in the polymer coatings of the invention is obtained when the value of (1+cos θ) is less than 0.55, preferably less than 0.50 and most preferably less than 0.0.48 or 0.45.

A good comparison of relative water and oil repellency can be obtained by determining and comparing the receding contact angle of various coatings. The receding contact angle measurement is more important than the advancing contact angle, because the advancing contact angle does not reflect surface energy changes as well as does the receding angle. Small changes in surface free energy can be easily detected by changes in receding contact angle values. As the energy increases the receding contact angle increases.

Articles coated with the polymers, such as fibers, fabrics, filter media, papers, films and membranes or the like, are also a part of the invention.

DETAILED DESCRIPTION OF THE INVENTION

It is believed that the increased crystallinity results in a polymer in which the side chains are stable and fixed, thus resisting movement when subjected to repeated water treatment. The initial water repellency is not only improved, but the water repellency is retained as well, as shown in Examples 4 and 5 below.

Literature references teach that receding contact angles are good means of measuring pockets of high energy in a largely hydrophobic surface. (Practicing Polymer Surface Chemistry—A Stream of Consciousness by David Dwight, Chemtech, March 1982). Receding contact angle data is a better measure of the wetability of a hydrophobic surface than advancing angle data because as described above, the advancing angle does not reflect surface energy changes as well. Furthermore, the 1+cos θ value of the receding contact angle is more demonstrative than the angle value itself inasmuch as it is directly proportional to energy levels of the polymer. Also, it is known that as the receding contact angle value approaches the advancing contact angle value, it is an indication that the surface free energy of the substrate surface is uniform over the surface. This is reflected in Table 2 where it is seen that with polymers of the invention the receding contact angle values are higher and closer to the advancing contact angle values than in polymers not of the invention.

Thus, the data in Table 2 shows that the polymers of the invention are less vulnerable to wet out since the receding contact angle values are higher, and thus the 1+cos θ values are lower, than for polymers not of the invention. When the coating contains pendant chains with —$CF_3$ end groups, this means good uniformity of low surface energy (i.e., high oil and water repellency). Good repellancy and durability is obtained when the 1+cos θ values of the receding contact angle are less than 0.55. Higher than this value indicates presence of less desirable fluoroalkyl configurations and thus more vulnerability to surface wet out. These wet out zones will hold water drops and this change in local environment will eventually cause a surface modification.

The stability of the surface of the polymer coatings of the invention as shown in Examples 4 and 5. In Example 4 the slower rate of loss of receding contact angle in water over time compared to the commercial sample is evident. It should be noted that the receding contact angle below 90° is equivalent to failure in the commercially used spray rating test with values less than 100, which is described in AATCC Tech Manual (199) Test Method 42-1989.

In this invention the fluoroalkyl side chain length is chosen to enhance formation of crystalline regions, thus resulting in close packing by aligning the side chains. By this means, the —$CF_3$ end groups maintain an effective barrier against water or oil penetration.

The monomers of this invention can be any organic monomer which, when polymerized, results in a polymeric backbone having perfluoroalkyl side chains depending from each repeat unit of the organic backbone. Representative of such monomers include polyacrylate, polymethacrylate, and their copolymers; polysiloxane and its copolymers; hydroxyl terminated organosiloxanes; polyurethane, polyurea and their copolymers; and any polymer backbone with urethane or urea groups incorporated in its side chain; polyamide and its copolymers; polyimide and its copolymers; sulfonate polymers; polyether glycols and their copolymers; polyolefin, polyalkylene and its copolymers; fluorocarbon polymers such as polytetrafluoroethylene; polystyrene derivatives and their copolymers; polyvinyl ether and its copolymers; polymethylenecyclopropane; polyacetylene and its copolymers; polysaccharide and its copolymers; polyvinylacetate and its copolymers; butadiene/styrene copolymers; polyoxazoline and its copolymers; poly(N-vinylimine) and its copolymers; poly(maleic or fumaric)anhydride and its copolymers; and the like.

The acrylate or methacrylate monomers of this invention can be prepared by reacting a perfluoroalkyl iodide with an unsaturated primary alkyl alcohol. The perfluoroalkyl iodide $F(CF_2)_nI$ is chosen so that n=10 is the predominate side chain length. The unsaturated alkyl primary alcohol has a preselected number of m carbon atoms as in $CH_2$=CH $(CH_2)_m$OH. The iodinated addition product is treated with Zn+HCl to remove the iodine and reduce the unsaturated carbon bonds to the saturated fluoroalkyl alcohol. An alternate method to obtain this fluoroalkyl alcohol is to first treat the addition product with potassium hydroxide in ethanol to remove the iodide ion (KI) followed by reduction of the olefin using hydrogen and platinum oxide catalyst or palladium on carbon. The acrylic ester is then formed from the alcohol with acryloyl chloride or acrylic acid.

Polymerization is carried out by polymerizing the monomer in a free radical polymerization and isolating the polymer formed.

The acrylate and methacrylate monomers of the invention can be polymerized in an appropriate organic solvent, such as hexafluoroxylene, dimethyl formamide, or by emulsion polymerization in water.

Coating of polymers on a substrate is ordinarily achieved from a solution or from the aqueous emulsion. The solution or emulsion can be also incorporated into a matrix which allows it to migrate to the surface.

The substrate can be a fabric, such as a nonwoven, woven, knit, or scrim. It will normally have interstices or passageways or pores that permit flow of fluids and can be used for garments; coverings (e.g. furniture or floor), or as filter media. The substrate can be a fiber. The substrate can also be a polymeric film or membrane, especially ones where pores form interstices or passageways. By "pores" or "porous" is meant that the film or membrane has continuous passageways through its thickness from one side to the other. The fabric, fiber, film or membrane can be made of polymeric materials, such as polyamide, polyester, polyvinylidene fluoride, polyacrylic, polyolefins such as polyethylene and polypropylene, porous polytetrafluoroethylene, especially microporous expanded polytetrafluoroethylene, and the like. Exemplification includes; for example, fiber weaves, or knits, glass, paper, e.g. filter paper, wood, leather, fur, asbestos, brick, concrete, metal, ceramics, plastics, painted surfaces, and plasters. Examples of manufactured fiber weaves include cotton, flax, wool, silk, and other plant and animal natural fibers. Examples also include synthetics, such as polyamide, polyester, polyvinyl alcohol, polyacrylonitrile, polyvinyl chloride, polypropylene, rayon, acetate, semi-synthetic fibers, glass fibers, asbestos fibers, and other inorganic fibers.

The water and oil repellents of the present invention are useful as a stainproofing agent, and can be used with carpets, sofas, curtains, wallpaper, and tents.

They are particularly useful in fabric constructions that have a waterproof, but vapor permeable barrier membrane as a part of the construction. Such constructions are useful as outerwear, e.g. coats, sweaters, shirts, etc. or underwear; and as hospital gowns or the like.

Tests on the polyacrylates and methacrylates of the invention show that the crystallizable side chains enhance repellency performance of the polymer. The polymers have lower receding contact angle 1+cos θ values when compared with commercial acrylate polymer samples. It is believed this is related to the stable packing of the fluorocarbon crystallizable side chains of the polymers of the invention, preventing molecular rearrangement in a water environment. As described above, receding contact angle measurements provide an indication of the surface free energy and thus in turn, the effectiveness of the coating as an oil and water repellent.

Durable repellency of the polymer coatings of the invention when tested in water at elevated temperatures is good. A fabric was coated with one commercial polymer, namely Milease (F-95) of Asahi Glass, (which is believed to be a copolymer with an acrylate backbone and side chains of both perfluoroalkyl groups and alkyl groups in about 80:20 ratio), and in which n is predomately 8 and m is 2 as analyzed by hydrolysis of the side chains followed by gas chromatography/mass spectroscopy (GC/MS). The coated fabric was soaked in water at room temperature, and exhibited a significant loss in repellency in less than 24 hours. On the other hand, a fabric coated with a polymer of the invention (having crystalline side chains) showed durability by remaining repellent for at least 50 hours.

The monomers of the invention can be homopolymerized or copolymerized. For copolymers, acrylates and methacrylates with alkyl side chains are preferred as the comonomer, but olefins or vinyl ethers, vinyl esters, or vinyl chloride, acrylamides, acrylonitrile, acrylic acid can also be employed. Preferably the amount of the comonomer present will not substantially reduce the water repellency or the durability imparted by the side chains.

The water and oil repellent polymers and copolymers may contain various crosslinking monomers. There is a wide range of such crosslinking monomers, including monomers having functional groups that can form covalent bonds through an addition or condensation reaction with the material to be treated, and monomers having functional groups, that can cure three-dimensionally through the action of a curing catalyst or the like. Examples include N-methylol acrylamide, N-methylol methacrylamide, N (isobutoxymethyl) acrylamide, glycidyl acrylate, glycidyl methacrylate, aziridinyl acrylate, aziridinyl methacrylate, diacetone acrylamide, diacetone methacrylamide, methylolated diacetone acrylamide, methylolated diacetone methacrylamide, ethylene diacrylate, ethylene dimethacrylate, hydroxyalkyl acrylate, and hydroxyalkyl methacrylate.

TEST PROCEDURES

Polymer Melting Point Determination

Test samples were enclosed in standard aluminum DSC pans. Pans were placed in the DSC cell of a TA Instrument Model DSC 2910 purged with helium gas. An empty standard pan was used as reference. The sample was heated from 0° C. to 150° C. at 10° C./minute. Heat flow was stored in the memory versus sample temperature. The heat flow was plotted versus sample temperature.

Sample melting is observed as an endotherm valley in the heating curve. The melting point was taken as the temperature of the valley minimum.

The DSC was temperature-calibrated per manufacturer's instruction.

Fluorocarbon Chain Distribution

Gas chromatography with mass and infrared detectors was used to determine the distribution of fluorocarbon chain lengths in the mixture of monomers to be polymerized, i.e., to determine the amount of monomer of a specific fluorocarbon chain length in the mixture of monomers. The area of each of the monomer peaks was determined as a percentage of the total area measured by chromatography. The area percentages of the monomer peaks were then normalized to 100% to determine the relative distribution between the monomers.

The samples were prepared as 1% ethyl ether solutions. A 1 micron liter solution was injected into the splitless injector of a GC instrument which was a Hewlett Packard Model 5890. The GC temperature program consisted of a warm-up of an initial temperature of 35° C. which was held for 5 minutes, followed by increasing the temperature at a rate of 10° C./minute to 265° C., and then maintaining the temperature at 265° C. for 20 minutes.

The column used was 25 meters HP-5 (5% phenyl silicone, 95% methyl silicone) with a 0.32 mm i.d. and 0.52 mm film thickness.

The data were used to determine the percentage of each $(CF_2)_nF$ entity present.

Dynamic Contact Angle Analysis (DCA) of Coatings

Coated monofilament samples are suspended by a clip on the electronic balance of a Cahn Dynamic Contact Angle Analyzer Model DCA-322. Below the sample is a 100 ml. beaker of distilled water of known surface tension. Cloister® brand distilled water (Cloister Spring Water Co.) was used having a surface tension at room temperature of 74° C. Other sources of water may give slightly different absolute contact angle values. The beaker of water is raised at a rate of 82.86 microns/second, immersing the sample to a depth of 10 millimeters. The force on the monofilament at any point along the surface is measured versus the distance of the filament's immersion. With the software provided by the manufacturer the force on the coated filament is converted to advancing and receding contact angle. Consistent with the Young-DuPre' equation, this data was transferred to 1+cos θ values because 1+cos θ is directly proportional to energy levels.

EXAMPLES

Example 1

Synthesis of $CH_2=C(CH_3)-CO-O-(CH_2)_m(CF_2)_nF$ a) Preparation of $F(CF_2)_nCH=CH(CH_2)_8OH$ Perfluoroalkyl iodide obtained from DuPont was used. Using the procedure set forth above, it was determined to have a carbon chain distribution containing C6 to C18. The iodide was distilled to remove the C6 and C8 content. This produced a composition of C8 (0.6%), C10 (64%), C12 (25%), C14 (8%), C16(2%) and C18 (0.6%), as determined by GC/MS. The starting iodide was also purchased from Hoechst already free of fractions lower than C10. The iodide; 139.3 g., 0.2004 moles, was charged to a 500 ml reaction vessel equipped with a condenser, magnetic stirrer, nitrogen atmosphere and a temperature controlled oil bath. 9-decen-1-ol (47 g, 0.3006 moles) from Penta Corp. was added. Temperature of the oil bath was adjusted to 95° C. To the melted mixture, azobisisobutyronitrile (AIBN) (1.20 g, 0.0073 moles) in 10 ml of tetrahydrofuran (THF) was syringed into the vessel slowly. The solution was then stirred at 95° C. under nitrogen for 3 hours. KOH (25.0 g, 0.4456 moles) dissolved in 120 ml of ethanol was added into the vessel dropwise with a dropping funnel over 30 minutes. The mixture was then stirred at 95° C. for another 2 hours.

The mixture was transferred into a 2-liter separatory funnel and washed with water and acidified with HCl to neutralize the solution. The product was extracted with diethyl ether twice. The combined ether portions were washed with water three times, dried over $MgSO_4$, filtered and the filtrate evaporated, leaving 140 g of solid. The solid was recrystallized in toluene once to give 76 g of pale soft needle-like crystals as the desired product.

b) Hydrogenation of the Alcohol

The alcohol of Part a) (68.4 g) was charged to an autoclave with 1 liter of ethanol (denatured with isopropanol), 20 ml of water and 0.76 g of platinum oxide. After purging the autoclave with hydrogen, it was pressurized to 50 psig with hydrogen. The autoclave was heated to 90° C. and stirred with a gas dispersive agitator at 1020 rpm. After 8 hours, the reaction mixture was pressured into a 2 liter flask, diluted with 600 ml ether and filtered to remove the catalyst. After the ether was removed from the filtrate by evaporation, the remaining ethanolic solution was poured into water to precipitate the product. The product was filtered and dried in vacuo at 60° C., 50 g was recovered. Gas chromotography/mass spectroscopy analysis (GC/MS) indicated that hydrogenation was complete.

c) Acrylation of the Hydrogenated Alcohol

A one liter reaction flask equipped with a nitrogen inlet, reflux condenser, syringe port and mechanical agitator was charged with 500 ml of dry THF by transfer needle. Next, was charged 65 g of the fluoroalcohol (0.093 moles), 14.3 ml of triethyl amine (20% molar excess) and 0.6 g hydroquinone. This mixture was heated by an oil bath to 40° C. with agitation before a solution was obtained. At this point, 11 ml of acryloyl chloride (20% molar excess) was syringed into the reaction mixture over 10 minutes. A precipitate formed almost immediately. The reaction mixture temperature was increased to 65° C. and was agitated for 5 hours. After cooling, the mixture was poured into 1.5 liter of water. The slightly acidic solution was neutralized with a 10% $NaCO_3$ solution. After several hours of standing, the precipitate was filtered and washed with copious amounts of water, and dried in vacuo, 50 g yield. The white crystalline powder obtained had amp of 95.8° C.

Example 2

Synthesis of Other Fluoroacrylates and Polymers made from the Monomers

Other fluoroacrylates containing side chains of specific length were prepared generally as above, using the corresponding alcohols purchased from PCR Corp.

Specifically, other fluoroacrylates prepared were ones having the formula

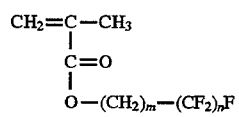

In this formula, the m numerical value for the samples listed in Table 1 following is the value set forth as determined in the section above titled Fluorocarbon Chain Distribution.

TABLE 1

| | Monomer Distribution | |
|---|---|---|
| m | n | Weight of Monomer Distribution In Mixture |
| 1. 2 | 8 | 100 |
| 2. 2 | 10 | 100 |
| 3. 2 | 8, 10, 12, 14 | 16, 59, 20, 5 |
| 4. 2 | 8, 10, 12 | 54, 34, 12 |
| 5. 6 | 10, 12, 14 | 66, 29, 5 |
| 6. 10 | 8 | 100 |
| 7. 10 | 8, 10, 12 | 54, 34, 12 |
| 8. 10 | 10, 12, 14 | 48, 39, 13 |
| 9. 2 | 8, 10, 12 | 54, 34, 12 |
| *10. 10 | 10 | 100 |
| *11. 10 | 10, 12, 14 | 63, 28, 9 |
| *12. 10 | 10, 12, 14 | 70, 30, 3 |
| *13. 10 | 10, 12, 14 | 67, 27, 3 |

*Representative of polymers of the invention.
9 is a commercial fluoroacrylate polymer, Milease F-95 from Asahi Glass. It is believed to contain a copolymer which in addition to the listed monomers contains 20% by weight units of:

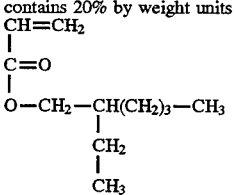

12 is a copolymer with 50% dodecyl acrylate units.

The m values are set forth based on starting material used; the n distribution of side chain lengths is based on monomer analysis by GC/MS, or based on vendor supplied data.

To make polymers, a 10% solution of a fluoroalkylacrylate monomer of Table 1 in hexafluoroxylene with 0.2 mole % of AIBN initiator was charged to a 100 ml reaction vessel which had been dried and swept with nitrogen. Polymerization was carried out at 60° C. for nominally 15 hours. The reaction mixture was then poured into methanol to precipitate the polymer. It was reprecipitated to ensure removal of monomer. Molecular weight of the polymers was carried out by size exclusion chromatography (SEC) using hexafluoroxylene as the mobile phase. Molecular weights ranged around 500,000.

Example 3

Sample Preparation For Contact Angle Measurement and Melting Point of a Polymer

The polymer samples were coated on nylon 6 monofilament with a circumference (or perimeter) of 2.69 mm. 20 mm sections of the monofilament were first cleaned with ethanol and dried in a forced air oven at 130° C. This was followed by dipping the monofilament three times in a 2% polymer solution with hexafluoroxylene as the solvent. It was generally required to warm the solution to 35° C. to maintain solution. The solvent was evaporated in a hood and the coated filament was heated in a forced air oven at about 160° C. for at least 3 minutes. This procedure was repeated as necessary in order to have a smooth continuous film as determined by Dynamic Contact Angle Measurements.

Dynamic Contact Angle Analyses were carried out on a Cahn DCA Instrument to measure advancing and receding contact angle of the coating prepared. Water was used as the liquid and the test was run at room temperature.

Melting points were determined by DSC.

Table 2 provides melting point, contact angle and hysteresis data for the homopolymers of the monomers of Table 1.

Example 4

Coated nylon 6 monofilaments of Example 3 were placed in distilled water at room temperature and contact angle measurements made at 24, 48 and 64 hours.

Changes in contact angles were observed as follows:

| | | | Contact Angles (°) | |
|---|---|---|---|---|
| m | n | % distribution of n | Advancing | Receding |
| 10 | 10 | (100) | 133° | 106 24 hrs |
| | | | 128 | 100 48 hrs |
| | | | 127 | 90 64 hrs |
| 2 | 8, 10, 12 | (54, 34, 12) | 127 | 80 24 hrs |
| | | | 124 | 60 48 hrs |
| | | | 118 | 47 64 hrs |

It is seen that when the polymer contains n=8, the receding angle falls off more precipitously as time goes by than for n=10, m=10, a polymer of the invention, which means greater molecular rearrangement in the n=8 sample. Thus the sample of the invention exhibits greater stability of side chain configuration, i.e., less tendency to rearrange to a less effective repellent configuration.

Example 5

Treatment of Coated Filaments With Water at Elevated Temperatures

The coated nylon filaments were exposed to water at various temperatures for 1 minute, then allowed to stand at room temperature at ambient conditions for 2 minutes and then tested for receding contact angle.

TABLE 2

| | m | n | Wt. of Monomer Distribution. in Mixture | Melt. Point 0° C. | Advancing Contact Angle | Receding Contact Angle CA | 1+cosθ of receding contact angle |
|---|---|---|---|---|---|---|---|
| 1. | 2 | 8 | 100 | 51 | 125 | 76 | 1.24 |
| 2. | 2 | 10 | 100 | 118 | 125 | 103 | 1.78 |
| 3. | 2 | 8, 10, 12, 14 | 16, 59, 20, 5 | ? | 133 | 115 | 0.58 |
| 4. | 2 | 8, 10, 12 | 54, 34, 12 | 74 | 127 | 109 | 0.67 |
| 5. | 6 | 10, 12, 14 | 66, 29, 5 | 106 | 139 | 113 | 0.61 |
| 6. | 10 | 8 | 100 | 46 | 128 | 109 | 0.67 |
| 7. | 10 | 8, 10, 12 | 54, 34, 12 | ? | 130 | 112 | 0.63 |
| 8. | 10 | 10, 12, 14 | 48, 39, 13 | 116 | 130 | 90 | 1.00 |
| 9. | 2 | 8, 10, 12 | 54, 34, 12 | 118/130 | 125 | 98 | 0.86 |
| *10. | 10 | 10 | 100 | 96 | 132 | 124 | 0.44 |
| *11. | 10 | 10, 12, 14 | 63, 28, 9 | 99 | 128 | 122 | 0.47 |
| *12. | 10 | 10, 12, 14 | 70, 30, 3 | 105 | 134 | 120 | 0.50 |
| *13. | 10 | 10, 12, 14 | 67, 27, 3 | — | 135 | 118 | 0.53 |

*Representative of the invention.
9 is the commercial fluoroacrylate polymer, Milease F-95, identified in Table 1.

It is seen that the (1+cos θ) values for samples 10–13 are quite low indicating more stability of the fluoroalkyl side chains, i.e., is less side chain mobility.

As for melting point, the higher the melting point, the greater the stability of the fluorocarbon side chain and thus the less the susceptibility to movement or rotation of the side chain. But if the melting point is too high it is difficult to process the polymers. A preferred melting point range is between 80° C. and 150° C., and more preferably between 90° C. and 110° C.

| | | | \multicolumn{6}{c}{Variation of Receding Contact Angle (Degrees) with Temperature Change} |
|---|---|---|---|---|---|---|---|---|
| | | | \multicolumn{6}{c}{Temperature (°C.)} |
| m | n | % Distribution of n | 25 | 40 | 50 | 60 | 80 | 95 |
| 2 | 8, 10, 12 | 54, 34, 12 | 109 | 107 | 100 | 94 | 90 | 89 |
| 10 | 8, 10, 12 | 54, 34, 12 | 112 | 95 | 85 | 81 | | |
| **2 | 8, 10, 12 | 54, 34, 12 | 95 | 90 | 80 | 68 | 30 | |
| 6 | 10, 12, 14 | 66, 29, 5 | 113 | — | — | 80.1 | 90.6 | 86.2 |
| 10 | 10, 12, 14 | 60, 30, 10 | 111 | — | — | 102 | 97 | 99 |
| *10 | 10 | 100 | 124 | 121 | 120 | 119 | 117 | 112 |

*A polymer of the invention.
**F-95

The individual temperatures are based on interpolated values to an average temperature.

It is seen that the receding angle tends to decrease less for the polymer of the invention as the water temperature increases. This means less molecular rearrangement in that sample.

We claim:

1. An organic polymer containing recurring units derived from organic monomers which have a segment in each monomer of the formula:

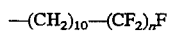

wherein n is a mixture of integers of 10 and more, in which the amount of the monomer containing the moiety:

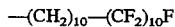

constitutes at least 50% or more of the total weight of all such monomers whose units are present in the polymer.

2. The organic polymer of claim 1 wherein the organic monomers that the polymer is derived from are acrylate or methacrylate monomers.

3. The organic polymer of claim 1 in the form of a liquid emulsion or solution of the polymer.

4. The organic polymer of claim 2 in which the melting point of the polymer is between 80° C. and 150° C. and in which the 1+cos θ value of the receding contact angle is less than 0.55.

5. The organic polymer of claim 4 in the form of a liquid emulsion or solution of the polymer.

6. The organic polymer of claim 4 wherein the recurring units are all derived from acrylate or methacrylate monomers.

7. Process for coating an article with a polymer of claim 1 which comprises applying said polymer to the surface of an article.

8. Process of claim 7 wherein the article is selected from the class consisting of fibers, fabrics, filter media, films and membranes.

9. Process for coating an article with a polymer of claim 4 which comprises applying said polymer to the surface of an article.

10. Process of claim 9 wherein the article is selected from the class consisting of fibers, fabrics, filter media, films and membranes.

* * * * *